United States Patent [19]

Dunn et al.

[11] 3,962,230

[45] June 8, 1976

[54] P-HYDROXYMETHYL-PHENYLACETAMIDOCEPHALOSPORINS

[75] Inventors: George L. Dunn, Wayne; John R. E. Hoover, Glenside, both of Pa.

[73] Assignee: SmithKline & French Laboratories, Inc., Philadelphia, Pa.

[22] Filed: Feb. 25, 1975

[21] Appl. No.: 552,916

Related U.S. Application Data

[60] Division of Ser. No. 359,566, May 11, 1973, Pat. No. 3,891,634, which is a continuation-in-part of Ser. No. 262,903, June 14, 1972, Pat. No. 3,867,380, which is a continuation-in-part of Ser. No. 116,598, Feb. 18, 1971, abandoned, which is a continuation-in-part of Ser. No. 99,296, Dec. 17, 1970, abandoned, which is a continuation-in-part of Ser. No. 289,499, Dec. 15, 1972, Pat. No. 3,855,213, which is a continuation-in-part of Ser. No. 262,903, June 14, 1972, and Ser. No. 116,599, Feb. 18, 1971, abandoned.

[52] U.S. Cl. .............................. 260/243 C; 424/246
[51] Int. Cl.² ........................................ C07D 501/20
[58] Field of Search ................................ 260/243 C

[56] References Cited
UNITED STATES PATENTS

| | | | |
|---|---|---|---|
| 3,641,021 | 2/1972 | Ryan | 260/243 C |
| 3,759,904 | 9/1973 | Crase | 260/243 C |

*Primary Examiner*—Nicholas S. Rizzo
*Attorney, Agent, or Firm*—Alan D. Lourie; William H. Edgerton

[57] ABSTRACT

7-(p-Hydroxymethylphenylglycylamido)cephalosporins are prepared by acylating a 7-aminocephalosporin compound. The products have antibacterial activity.

3 Claims, No Drawings

P-HYDROXYMETHYL-PHENYLACETAMIDOCEPHALOSPORINS

This is a division of application Ser. No. 359,566 filed May 11, 1973 now U.S. Pat. No. 3,891,634 which is a continuation-in-part of application Ser. No. 262,903, filed June 14, 1972, now U.S. Pat. No. 3,867,380 which was a continuation-in-part of Ser. No. 116,598, filed Feb. 18, 1971, now abandoned, which was a continuation-in-part of Ser. No. 99,296, filed Dec. 17, 1970, now abandoned, and it is also a continuation-in-part of application Ser. No. 289,499 filed Sept. 15, 1972, now U.S. Ser. No. 3,855,213, which was continuation-in-part of Ser. No. 262,903, filed June 14, 1972 and of Ser. No. 116,599, filed Feb. 18, 1971, now abandoned, which latter application was a continuation-in-part of Ser. No. 99,296, filed Dec. 17, 1970, now abandoned.

This invention relates to cephalosporin compounds. In particular, the invention relates to p-hydroxymethyl-phenylacetamidocephalosporins of formula I

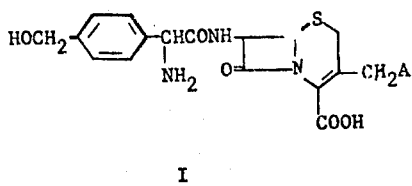

I wherein A is acetoxy, hydrogen, methoxy, methylthio, or monocyclic heterocyclic thio.

The invention also relates to a process for preparing the compounds of formula I comprising acylating a compound of the formula

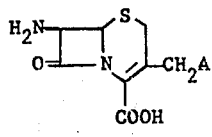

II wherein A is as defined above, with p-hydroxymethyl-phenylglycine, or an acylating or activated derivative thereof, the amino group being protected with an easily removable protecting group.

The invention also relates to intermediates for preparing the compounds of formula I, these intermediates being p-hydroxymethylphenylglycine and its N-t-butoxycarbonyl derivative.

Among the preferred compounds of the invention are those of formula I in which A is heterocyclic thio. Such preferred heterocyclic groups include 1,2,3-triazol-5-yl, 2-methyl-1,3,4-thiadiazol-5-yl, and 1-methyltetrazol-5-yl. Other such groups can be oxadiazolyl, 1,2,4-triazol-3-yl, and tetrazol-5-yl and methyl derivatives thereof. The term heterocyclic, however, is intended to represent any monocyclic heterocyclic group containing, in addition to one or more carbon atoms, one or more nitrogen, sulfur, or oxygen atoms and being either unsubstituted or substituted with one or more lower alkyl or alkoxy groups of one to four carbon atoms.

The product compounds of the invention are prepared by acylating the 7-amino group of a compound of formula II with p-hydroxymethylphenylglycine. This starting material is prepared by first reducing one of the aldehyde groups of 1,4-benzenedicarboxaldehyde with lithium tri(t-butoxy)-aluminum hydride, condensing the remaining aldehyde group of the resulting hydroxymethyl aldehyde with ammonium carbonate and sodium cyanide to give a hydantoin, and hydrolyzing the hydantoin with barium hydroxide.

Prior to acylation, it is desirable to protect the amino group on the glycine moiety with an easily removable protective group such as t-butoxycarbonyl, benzyloxycarbonyl, trichloroethoxycarbonyl, or similar protective group commonly used in the synthesis of peptides. The carboxyl group can be activated for acylation by conversion to the acid chloride or to a mixed anhydride with, for example, a lower alkyl chloroformate. It can also be activated by conversion to the 2,4-dinitrophenyl or N-hydroxysuccinimidyl esters. If an ester of the carboxyl group on the cephalosporin nucleus is used as an acylation substrate, e.g. a benzhydryl, t-butyl, trichloroethyl, or benzyl ester, the amine-protected phenylglycine can be coupled directly to the 7-amino group by using a carbodiimide such as dicyclohexylcarbodiimide. Alternatively, the protected phenylglycine can be activated for condensation by reacting it first with carbonyl diimidazole or its equivalent.

Following the acylation, the protective groups can be removed with an acid such as trifluoroacetic acid. The resulting salt is converted to the zwitterionic product by means of a basic ion exchange resin such as a polystyrene-amine ion exchange resin (Amberlite IR-45) or else by basification of an aqueous solution of the salt.

The compounds of formula I in which A is heterocyclic thio may also be prepared by first acylating 7-aminocephalosporanic acid (the compound of formula II in which A is acetoxy) with p-hydroxymethyl-phenylglycine and then displacing the acetoxy group with a heterocyclic thiol according to known methods. The compounds of formula I where R is methoxy or methylthio may also be prepared by first acylating 7-aminocephalosporanic acid and then inserting the methoxy or methylthio group by known methods.

The starting materials for the products of the invention, i.e. the compounds of formula II, are either known or are prepared by known methods, including displacement of the acetoxy group of 7-aminocephalosporanic acid with a heterocyclic thiol, also by known methods.

The compounds of the invention are highly active as antibacterial agents. They are formulated into injectable and oral dosage formulations such as solutions, suspensions, tablets, and capsules in the same manner as are other cephalosporin antibiotics and are administered by injection or orally to prevent and treat bacterial infections. The doses will vary with the age, weight, and condition of the subject and are determinable by those skilled in the art based on data presented herein and experience with other cephalosporins.

Data for a number of compounds of the invention follow:

| No. | COMPOUND IDENTIFICATION A |
|---|---|
| 47216 | H |
| 37316 | $OCOCH_3$ |
| 62516 | (N—N heterocyclic thio with $CH_3$) |

-continued
COMPOUND IDENTIFICATION

| No. | A |
|---|---|
| 43026 | (structure: -S-[triazole-NH]) |
| 76026 | (structure: -S-[triazole-N-CH₃]) |

| Compound No. | S. aureus | S. aureus | MIC/μg/ml Strep. faecalis | E. coli | E. coli | Klebs. pneumo. | Klebs. pneumo. |
|---|---|---|---|---|---|---|---|
| 47216 | 6.3 | 25 | | 25 | 50 | 25 | 25 |
| 37316 | 12.5 | 6.3 | 200 | 12.5 | 25 | 3.1 | 25 |
| | | | 200 | 50 | 25 | 25 | |
| 62516 | 25 | 12.5 | 200 | 25 | 25 | 12.5 | 12.5 |
| | 3.1 | 6.3 | 100 | 12.5 | 12.5 | 6.3 | 6.3 |
| 43026 | 12.5 | 3.1 | 200 | 12.5 | 12.5 | 12.5 | 12.5 |
| 76026 | 50 | 50 | >200 | 25 | 50 | 25 | 25 |

| Compound No. | Pseudomonas sp. | Salmonella | MIC/μg/me Shigella | Entero. aerog. | Serratia marc. | Staph. Villaluz |
|---|---|---|---|---|---|---|
| 47216 | >200 | 25 | 25 | 50 | >200 | 200 |
| 37316 | >200 | 12.5 | 6.3 | 25 | >200 | 100 |
| | >200 | 25 | 25 | 200 | >200 | 100 |
| 62516 | | 12.5 | 12.5 | 50 | >200 | 200 |
| | >200 | 3.1 | 6.3 | 25 | >200 | 50 |
| 43026 | >200 | 6.3 | 6.3 | 25 | >200 | 50 |
| 76026 | >200 | 25 | 25 | 50 | >200 | 200 |

| Compound No. | E. coli s.c. | ED₅₀ (mg/kg.) p.o. | Klebs. pneumo. s.c. | p.o. |
|---|---|---|---|---|
| 47216 | 33 | 29 | >50 | 50 |
| 37316 | 8.7 | >50 | 20 | >50 |
| 62516 | 17, 25 | 39, 46 | 12.5, 17 | 18, 14.5 |
| 43026 | 11, 11.2 | 7.4, 21 | 14.5, 7.2 | 8.3, 6.2 |
| 76026 | 8 | 25 | 9.5, 7 | 16.7, <12.5 |

Due to the presence of both an amine group and a carboxylic acid group in the product compounds of the invention, it is possible to prepare both acid and base salts as well as zwitterionic forms of the compounds. Salts when obtained are readily converted to the zwitterions by known methods. The zwitterions in turn are readily converted into conventional acid and basic salts. It is understood that all these salts are included within the scope of the invention.

It is recognized that, due to the asymmetric α-carbonatom in the 7-acetamido group, optical isomers will exist. While the D-isomer is preferred, the L-isomer and the racemic mixtures are also within the scope of the invention. The isomers are obtained from racemic mixtures by conventional resolution techniques supplied to the intermediate side chain before acylation or the final product.

The following examples are intended to illustrate the products and processes of the invention, but are not to be contrued as limiting the scope thereof. Temperatures are in degrees Centigrade unless otherwise stated.

EXAMPLE 1

7β-(DL-α-Amino-p-hydroxymethylphenylacetamido)-desacetoxycephalosporanic acid To a solution of 1,4-benzenedicarboxaldehyde (50.0 g., 0.373 mole) in 200 ml. of dry tetrahydrofuran under nitrogen in an ice bath was added dropwise lithium tri(t-butoxy)aluminum hydride (104.0 g., 0.410 mole) dissolved in 500 ml. of dry tetrahydrofuran. After stirring for one half hour in an ice bath, the reaction mixture was poured into 2 l. of ice cold 2N hydrochloric acid. The aqueous solution was extracted with four 800 ml portions of ether. The combined ether layers were washed with 500 ml of ice cold 5% sodium bicarbonate solution and then with 500 ml of saturated sodium chloride solution. After drying, the ether was removed under reduced pressure to give 46 g. of crude p-hydroxymethylbenzaldehyde. The crude product was chromatographed over 1 kg of neutral alumina and the fractions eluted with ether and concentrated. Upon cooling there crystallized out p-hydroxymethylbenzaldehyde (17.6 g., 35% yield), m.p. 44.5°–46°C.

To a stirred mixture of Phydroxyme thylbenzaldehyde (10.0g, 0.0735 mole) and ammonium carbonate (17.1g, 0.15 mole) in 110 ml of 60% ethanol heated to 50°C there was added dropwise sodium cyanide (4.0g., 0.081 mole) dissolved in 10 ml water. The mixture was stirred and heated to 55°–60°C for 3 hours and then the temperature raised to 85°C for 1 hour. After cooling in an icebath, the pH of the solution was brought to 6 by the addition of concentrated hydrochloric acid. Upon overnight cooling, the solid which had precipitated was filtered, washed with cold water, and dried. The 5-(p-hydroxymethylphenyl)hydantoin (11.0g., 72% yield), m.p. 189°–196° (dec.), was used to prepare the amino acid without further purification.

A mixture of 5-(p-hydroxymethylphenyl) hydantoin (10.9 g., 0.053 mole) and barium hydroxide (8.H₂O) (25.5 g, 0.081 mole) in 125 ml water was stirred and refluxed for 18 hours. After cooling in an ice bath the reaction mixture was diluted with 125 ml water. The solution was acidified with concentrated sulfuric acid to pH 1, the barium sulfate filtered, and the pH of the filtrate brought to 6 with lead carbonate. After filtration of the lead sulfate, the filtrate was saturated with hydrogen sulfide and the lead sulfide filtered. The aqueous solution was then concentrated to 100 ml by azeotroping with ethanol under reduced pressure. After cooling, there was precipitated p-hydroxymethylphenylglycine (5.2 g., 54% yield) m.p. 228°–229°C (dec). After recrystallization from ethanol-water the compound had m.p. 230°–231° (dec.)

Calc'd for $C_9H_{11}NO_3$: C, 59.66; H, 6.12; N, 7.73. Found: C, 59.46; H, 6.24; N, 7.93.

To a solution of p-hydroxymethylphenylglycine (8.0 g, 0.044 mole) and triethylamine (8.8 g., 0.087 mole) in 160 ml water was added t-butoxycarbonyl azide (6.95 g., 0.049 mole) dissolved in 120 ml tetrahydrofuran. After stirring overnight at room temperature, the reaction mixture was washed twice with 200 ml. portions of ether. The aqueous layer was covered with ether and in an ice bath was acidified to pH 3–3.5 with 3N hydrochloric acid. The acidic solution was extracted three times with 200 ml portions of ether. The combined ether layers were washed with saturated sodium chloride solution, dried, and the ether evaporated under reduced pressure. The resulting oil was triturated with chloroform-hexane and the solid filtered off to give N-t-butoxycarbonyl-p-hydroxymethylphenylglycine (7.74 g, 63% yield), m.p. 139°–141.5° (dec.).

Calc'd for $C_{14}H_{19}NO_5$: C, 59.78; H, 6.81; N, 4.98. Found: C, 59.67; H, 6.76; N, 4.69.

dl-N-t-Butoxycarbonyl-p-hydroxymethylphenylglycine (7.560 g, 0.0269 mole) and quinine (10.199 g, 0.0269 mole) were mixed and dissolved in 110 ml of boiling ethanol. The solution was allowed to cool to room temperature and to crystallize overnight. The salt was filtered off and the crystallization repeated three times.

The salt (17.76 g, m.p. 198°–201° dec., $[\alpha]_D^{25}$ −149.8, C=1, $CH_3OH$) gave after three recrystallizations resolved salt (4.6 g, m.p. 205°–6° dec., $[\alpha]_D^{25}$ −163.4, C=1, $CH_3OH$). An additional recrystallization did not increase the optical rotation.

The (−) quinine salt of (−) N-t-butoxycarbonyl-p-hydroxymethylphenylglycine was suspended in 75 ml. water and 175 ml ether in an ice bath and 3N hydrochloric acid added to pH 2.5. The ether layer was removed and the aqueous layer extracted twice with 100 ml portions of ether. The combined ether layers were washed with 100 ml saturated sodium chloride, dried, and the ether removed under reduced pressure. The residue was triturated with chloroform-hexane and filtered to give D (−) N-t-butoxycarbonyl-p-hydroxymethylphenylglycine (1.68 g, 98% recovery), m.p. 111°–113.5° dec., $[\alpha]_D^{25}$ = −136.5 (C=1, $CH_3OH$).

To a solution of dl-N-butoxycarbonyl-p-hydroxymethylphenylglycine (3.0 g, 0.011 mole) and N-hydroxy-succinimide (1.25 g., 0.011 mole) in 10 ml dry tetrahydrofuran and 50 ml dry acetonitrile was added N,N'-dicyclohexyl-carbodiimide (2.238 g., 0.011 mole). The mixture was stirred at room temperature overnight. The dicyclohexylurea was filtered off and the filtrate taken to dryness under reduced pressure. The resulting solid was triturated with ether and filtered to give the N-hydroxysuccinimide ester of N-t-butoxycarbonyl-p-hydroxyphenylglycine (3.4 g., 83% yield) m.p. 141°–148° dec.

When D(−)-N-t-butoxycarbonyl-p-hydroxymethylphenylglycine was used, the corresponding optically active ester was obtained: m.p. 86°–90° dec; $[\alpha]_D^{25}$ = −47.6 (C 1, MeOH).

N,N'-dicyclohexylcarbodiimide (0.363 g., 1.76 mmole) was added with stirring to a solution of N-t-butoxycarbonyl-p-hydroxymethylphenylglycine (0.452 g, 1.61 mmole) and 7-aminodesacetoxycephalosporanic acid, t-butyl ester (0.434 g, 1.61 mmole) in 5 ml tetrahydrofuran and 5 ml acetonitrile at 0°C. The reaction mixture was warmed to room temperature and stirred overnight. Methylene chloride (10 ml) was added to the mixture and the N,N'-dicyclohexylurea was filtered off and washed with methylene chloride. The filtrate was washed with ice cold 1% phosphoric acid, with ice cold 1% sodium bicarbonate and then with saturated sodium chloride solution. The dried filtrate was chromatographed over silica gel, and the fractions eluted with methylene chloride-ethyl acetate were combined and taken to dryness. The residue was triturated with ether and filtered to give 7β-(DL-α-N-t-butoxycarbonylamino-p-hydroxymethyl-phenylacetamido)desacetoxycephalosporanic acid, t-butyl ester (0.638 g, 75% yield), m.p. 126°–130° dec.

Calc'd for $C_{26}H_{35}N_3O_7S \cdot \frac{1}{2}H_2O$: C, 57.55; H, 6.69; N, 7.74. Found: C, 57.96; H, 6.45; N, 7.89.

To a solution of 7 ml trifluoroacetic acid containing 8 drops of anisole at 0°C was added 7β-(DL-α-N-t-butoxycarbonylamino-p-hydroxymethyl-phenylacetamido)-desacetoxycephalosporanic acid, t-butyl ester (0.628 g., 1.2 mmole). The solution was stirred and maintained at 0°C for 1 hour. The trifluoroacetic acid was removed under reduced pressure and the residue triturated four times with ether. There was obtained 7β-(DL-α-amino-p-hydroxymethyl-phenylacetamido)desacetoxycephalosporanic acid, trifluoroacetate salt (0.51 g., 90% yield), m.p. 141°–170°C dec.

Calc'd. for $C_{19}F_3H_{20}N_2O_7S \cdot 1H_2O$: C, 44.79; H, 4.35; N, 8.25. Found: C, C, 44.97; H, 4.10; N, 8.02.

This salt is converted to the zwitterion by dissolving it in water and adding a polystyrene-amine ion exchange resin such as Amberlite IR-45. After stirring for about an hour at room temperature, the resin is filtered off and the aqueous solution lyophilized to give the title compound.

The trifluoroacetate salt can also be dissolved in water, methyl isobutyl ketone added, and tributylamine added to precipitate the zwitterion. The product is collected, washed, and dried.

EXAMPLE 2

7β-(DL-α-amino-p-hydroxymethylphenylacetamido)-cephalosporanic acid

N-t-butoxycarbonyl-p-hydroxymethylphenylglycine (0.60 g, 2.14 mmole), 7-aminocephalosporanic acid, t-butyl ester (0.705 g, 2.14 mmole) and N,N'-dicyclohexylcarbodiimide (0.485 g, 2.35 mmole) were reacted under the same conditions as in Example 1. After two chromatographies over silica gel and trituration with hexane there was obtained 7β-(DL-α-N-t-butoxycarbonylamino-p-hydroxymethylphenylacetamido)-cephalosporanic acid, t-butyl ester (0.238 g, 19% yield) m.p. 111°–115° dec.

Calc'd. for $C_{28}H_{37}N_3O_9S$: C, 56.84; H, 6.30; N, 7.10 Found: C, 57.65; H, 6.68; N, 6.71.

As in Example 1, 7β-(DL-α-N-t-butoxycarbonylamino-p-hydroxymethylphenylacetamido)cephalosporanic acid, t-butyl ester (0.222 g, 0.376 mmole) was added to ice cold trifluoroacetic acid and anisole. There was obtained 7β-(DL-α-amino-p-hydroxymethylphenylacetamide)cephalosporanic acid, trifluoroacetate salt (0.159 g., 77% yield) m.p. 136°–150° dec.

Calc'd. for $C_{21}F_3H_{22}N_3O_9S.\frac{1}{2}$ mole $H_2O$: C, 46.16; H, 4.15; N, 7.52. Found: C, 45.01; H, 3.95; N, 7.19.

The trifluoroacetate salt is converted to the title product as described in Example 1.

EXAMPLE 3

3-(1,2,3-Triazol-5-ylthiomethyl)-7β-(DL-α-amino-p-hydroxymethylphenylacetamido)-3-cephem-4-carboxylic acid 3-(1,2,3-Triazol-5-ylthiomethyl)-7-amino-3-cephem-4-carboxylic acid (0.60 g., 1.92 mmole) was dissolved with stirring in 12 ml dry pyridine containing triethylamine (0.39 g, 3.84 mmole) and to the solution was added the N-hydroxysuccinimide ester of N-t-butoxycarbonyl-p-hydroxymethylphenylglycine (0.73 g., 1.92 mmole). After stirring at room temperature for 4 hours, the reaction mixture was poured into 200 ml of ether and the precipitated solid filtered. The solid was dissolved in 100 ml of water and the water covered with ethyl acetate. This mixture was placed in an ice bath and acidified with 3N hydrochloric acid to pH2. Any solid was filtered off and the ethyl acetate layer removed and the aqueous layer extracted two times with ethyl acetate. The combined ethyl acetate layers were washed with saturated sodium chloride solution, dried, and the ethyl acetate was removed under reduced pressure. The residue was triturated with ether to give 3-(1,2,3-triazol-5-ylthiomethyl)-7β-(DL-α-N-t-butoxycarbonylamino-p-hydroxymethylphenylacetamido)-3-cephem-4-carboxylic acid (0.651 g, 59% yield) m.p. 197°–220° dec.

Calc'd. for $C_{24}H_{28}N_6O_7S_2.\frac{1}{2}$ $C_4H_{10}O$: C, 50.89; H, 5.42; N, 13.69. Found: C, 50.83; H, 5.69; N, 12.04.

When the resolved D(—) phenylglycine derivative was used, the product had m.p. 173°–198° dec.

3-(1,2,3-Triazol-5-ylthiomethyl)-7β-(DL-α-N-t-butoxycarbonylamino-p-hydroxymethylphenylacetamido)-3-cephem-4-carboxylic acid (0.570 g, 0.99 mmole) was added to 10 ml trifluoroacetic acid containing 2 ml anisole in an ice bath. The solution was stirred at 0°C. for ½ hour. The trifluoroacetic acid was removed under reduced pressure. The residue was triturated four times with ether to yield 3-(1,2,3-triazol-5-ylthiomethyl)-7β-(DL-α-amino-p-hydroxymethylphenylacetamido)-3-cephem-4-carboxylic acid, trifluoroacetate (0.44 g, 75% yield) m.p. 155°–162° dec.

Calc'd. for $C_{21}F_3H_{21}N_6O_7S_2$: C, 42.71; H, 3.58; N, 14.23. Found: C, 42.03; H, 3.67; N, 11.85.

When the pure diastereoisomer was used, the product obtained had m.p. 164°–170° dec.; $[\alpha]_D^{25} = -13.1$ (C 1, MeOH)

Analysis: $C_{21}F_3H_{21}N_6O_7S_2$. 1 mole $Et_2O$. Calc'd. for C, 45.18; H, 4.66; N, 12.65. Found: C, 45.53; H, 4.73; N, 11.26.

The salts are converted to their zwitterions as in Example 1.

EXAMPLE 4

3-(2-Methyl-1,3,4-thiadiazol-5-ylthiomethyl)-7β-(DL-α-amino-p-hydroxymethylphenylacetamido)-3-cephem-4-carboxylic acid 3-(2-Methyl-1,3,4-thiadiazol-5-thiomethyl)-7-amino-3-cephem-4-carboxylic acid (0.695 g, 2 mmole), the N-hydroxy succinimide ester of DL-N-t-butoxycarbonyl-p-hydroxymethylphenylglycine (0.760 g, 2 mmole) and triethylamine (0.41 g, 4 mmole) were reacted under the same conditions as in Example 3. After vaporation of the ethyl acetate the residue was triturated with hexane to yield 3-(2-methyl-1,3,4-thiadiazol-5-ylthiomethyl)-7β-(DL-α-N-t-butoxycarbonylamino-p-hydroxymethylphenylacetamido)-3-cephem-4-carboxylic acid (0.709 g, 59% yield) m.p. 129°–138° dec.

Calc'd. for $C_{25}H_{29}N_5O_7S_3$.1 mole EtOAc: C, 50.07; H, 5.32; N, 10.07. Found: C, 50.43; H, 5.46; N, 10.42.

3-(2-Methyl-1,3,4-thiadiazol-5-ylthiomethyl)-7β-(DL-α-N-t-butoxycarbonylamino-p-hydroxymethylphenylacetamido)-3-cephem-4-carboxylic acid (0.65 g, 1.1 mmole) was converted under the reaction conditions of Example 3 to 3-(2-methyl-1,3,4-thiadiazol-5-ylthiomethyl)-7β-(DL-α-amino-p-hydroxymethylphenylacetamido)-3-cephem- 4-carboxylic acid, trifluoroacetate (0.574 g, 85% yield) m.p. 142°–154° (dec.)

Calc'd for $C_{22}F_3H_{22}N_5O_7.\frac{1}{2}$ mole $H_2O.\frac{1}{2}$ mole $Et_2O$: C, 43.11; H, 4.34; N, 10.47. Found: C, 42.92; H, 4.07; N, 9.96.

The salt is converted to the zwitterion as in Example 1.

EXAMPLE 5

3-(1-Methyltetrazol-5-ylthiomethyl)-7β-(DL-α-N-t-butoxycarbonylamino-p-hydroxymethylphenylacetamido)-3-cephem-4-carboxylic acid 3-(1-Methyltetrazol-5-ylthiomethyl)-7-amino-3-cephem-4-carboxylic acid (1.22 g, 3.7 mmole), the N-hydroxysuccinimide ester of DL-N-t-butoxycarbonyl-p-hydroxymethylphenylglycine (1.40 g., 3.7 mmole) and triethylamine (0.75 g, 7.4 mmole) were reacted under the same conditions as in Example 3. After trituration with hexane, there was obtained 3-(1-methyltetrazol-5-ylthiomethyl)-7β-(DL-α-N-t-butoxycarbonylamino-p-hydroxymethylphenylacetamido)-3-cephem-4-carboxylic acid (1.3 g, 59% yield) m.p. 138°–148° dec.

Calc'd. for $C_{24}H_{29}N_7O_7S_2$.1 ½ mole EtOAc: C, 49.79; H, 5.67; N, 13.55. Found: C, 49.75; H, 5.78; N, 13.30.

3-(1-Methyltetrazol-5-ylthiomethyl)-7β-(DL-α-N-t-butoxycarbonylamino-p-hydroxymethylphenylacetamido)-3-cephem-4-carboxylic acid was converted under the conditions of Example 3 to 3-(1-methyltetrazol-5-ylthiomethyl)-7β-(DL-α-amino-p-hydroxymethylphenylacetamido)-3-cephem-4-carboxylic acid, trifluoroacetate salt (0.946 g, 71% yield) mp 158°–165° dec.

Calc'd for $C_{21}F_3H_{22}N_7O_7S_2$. 2 mole $H_2O.2$ mole $Et_2O$: C, 44.10; H, 5.36; N, 12.41. Found: C, 43.95; H, 4.65; N, 12.40.

The salt is converted to the zwitterion as in Example 1.

EXAMPLE 6

When the following 7-aminocephalosporin compounds are acylated according to the procedures of Examples 1–5, the corresponding 7-(α-amino-p-hydroxymethylphenylacetamido)-cephalosporin compounds are obtained:

7-amino-3-(5-methyl-1,2,4-triazol-3-ylthiomethyl)-3-cephem-4-carboxylic acid 7-amino-3-(1-methyl-1,2,3-triazol-5-ylthiomethyl)-3-cephem-4-carboxylic acid 7-amino-3-(4-methyl-1,2,3-triazol-5-ylthiomethyl)-3-cephem-4-carboxylic acid 7-amino-3-(tetrazol-5-ylthiomethyl)-3-cephem-carboxylic acid 7-amino-3-(2-methyl-1,3,4-oxadiazol-5-ylthiomethyl)-3-cephem-4-carboxylic acid 7-amino-3-(1,2,4-triazol-3-ylthiomethyl)-3-cephem-4-carboxylic acid 7-amino-3-methylthiomethyl-3-cephem-4-carboxylic acid 7-amino-3-methoxymethyl-3-cephem-4-carboxylic acid

EXAMPLE 7

For parenteral administration a pharmaceutical composition can be prepared by dissolving 500 mg. of sodium 7-(α-amino-p-hydroxymethylphenylacetamido)-3-(1,2,3-triazol-5-ylthiomethyl)-3-cephem-4-carboxylic acid in 2 ml. of sterile water or normal saline solution. Any of the other products disclosed herein may be formulated similarly, particularly the products of examples 1, 2, 4, and 5.

EXAMPLE 8

A capsule for oral administration may be prepared by mixing 500 mg. of a cephalosporin disclosed herein, product, particularly a product of examples 1–5, 250 mg. of lactose, and 75 mg. of magnesium stearate.

We claim:
1. A compound of the formula

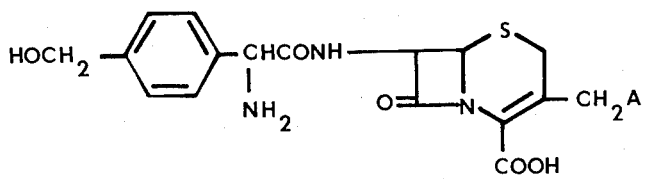

wherein A is methoxy or methylthio, or a pharmaceutically acceptable salt thereof.

2. A compound according to claim 1, being 7-(α-amino-p-hydroxymethylphenylacetamido)-3-methylthiomethyl-3-cephem-4-carboxylic acid.

3. A compound according to claim 1, being 7-(α-amino-p-hydroxymethylphenylacetamido)-3-methoxymethyl-3-cephem-4-carboxylic acid.

* * * * *